US012502333B2

(12) United States Patent
Converse et al.

(10) Patent No.: US 12,502,333 B2
(45) Date of Patent: Dec. 23, 2025

(54) MEDICAL FLUID INJECTION AND TRANSFER DEVICES AND METHOD

(71) Applicant: Enable Injections, Inc., Cincinnati, OH (US)

(72) Inventors: Rowan Joseph Converse, Liberty Township, OH (US); Matthew J. Huddleston, Loveland, OH (US); Daniel L. Geiger, Newport, KY (US); James Lowe, Cincinnati, OH (US); Richard P. Nuchols, Williamsburg, OH (US); David Stefanchik, Morrow, OH (US)

(73) Assignee: Enable Injections, Inc., Cincinnati, OH (US)

( * ) Notice: Subject to any disclaimer, the term of this patent is extended or adjusted under 35 U.S.C. 154(b) by 818 days.

(21) Appl. No.: 17/624,631

(22) PCT Filed: Jul. 24, 2020

(86) PCT No.: PCT/US2020/043515

§ 371 (c)(1),
(2) Date: Jan. 4, 2022

(87) PCT Pub. No.: WO2021/016567

PCT Pub. Date: Jan. 28, 2021

(65) Prior Publication Data

US 2022/0280385 A1 Sep. 8, 2022

Related U.S. Application Data

(60) Provisional application No. 62/878,111, filed on Jul. 24, 2019.

(51) Int. Cl.
*A61J 1/20* (2006.01)
*A61M 5/20* (2006.01)
(Continued)

(52) U.S. Cl.
CPC ............ *A61J 1/2003* (2015.05); *A61J 1/201* (2015.05); *A61J 1/2027* (2015.05); *A61J 1/2068* (2015.05);
(Continued)

(58) Field of Classification Search
CPC ......... A61M 2005/14252; A61M 2005/14513; A61M 5/155; A61M 5/152; A61M 5/1483;
(Continued)

(56) References Cited

U.S. PATENT DOCUMENTS 4,332,246 A * 6/1982 Thomson ............ A61M 5/1486 604/28
7,389,800 B2 * 6/2008 Hickman ............ B67D 7/0244 141/26
(Continued)

FOREIGN PATENT DOCUMENTS

EP 2893916 A1 7/2015
JP S58216056 A 12/1983
(Continued)

OTHER PUBLICATIONS

International Search Report and Written Opinion, counterpart International Appl. No. PCT/US2020/043515, (Nov. 26, 2020) (15 pages).
(Continued)

*Primary Examiner* — Quynh-Nhu H. Vu
(74) *Attorney, Agent, or Firm* — Cook Alex Ltd.

(57) ABSTRACT

A medical fluid injection device, a medical fluid transfer device and a method of administering and transferring a medical fluid are disclosed. The device and method may include a compressed gas canister in fluid communication with an expandable elastic bladder positioned within a vial of drug to provide a means to deliver drug through an
(Continued)

injection cannula that is movable between a plurality of positions or through a transfer conduit.

13 Claims, 15 Drawing Sheets

(51) Int. Cl.
*A61M 5/31* (2006.01)
*A61M 5/32* (2006.01)

(52) U.S. Cl.
CPC ........... *A61J 1/2086* (2015.05); *A61J 1/2096* (2013.01); *A61M 5/2046* (2013.01); *A61M 5/3145* (2013.01); *A61M 5/322* (2013.01); *A61M 2005/2013* (2013.01); *A61M 2005/2026* (2013.01); *A61M 2005/3114* (2013.01); *A61M 2005/3115* (2013.01); *A61M 2005/3123* (2013.01); *A61M 2005/3128* (2013.01)

(58) Field of Classification Search
CPC ................ A61M 5/148; A61M 5/1486; A61M 2005/2013; A61M 2005/2026; A61M 2005/3114; A61M 5/2046; A61J 1/2003; A61J 1/201; A61J 1/2006; A61J 1/2027; A61J 1/2096
See application file for complete search history.

(56) References Cited

U.S. PATENT DOCUMENTS

| | | | | |
|---|---|---|---|---|
| 7,547,300 | B2 * | 6/2009 | Fangrow | A61J 1/2082 604/71 |
| 2002/0055711 | A1 * | 5/2002 | Lavi | A61M 5/326 604/110 |
| 2006/0217662 | A1 | 9/2006 | Hickman et al. | |
| 2007/0244459 | A1 * | 10/2007 | Fangrow | A61J 1/1412 604/411 |
| 2008/0269713 | A1 | 10/2008 | Kavazov | |
| 2011/0073249 | A1 | 3/2011 | Fangrow | |
| 2012/0065609 | A1 | 3/2012 | Seifert et al. | |
| 2014/0174596 | A1 | 6/2014 | Lopez et al. | |
| 2015/0217058 | A1 * | 8/2015 | Hooven | A61M 5/145 604/403 |
| 2016/0144105 | A1 * | 5/2016 | Hooven | A61M 5/3157 604/132 |
| 2016/0175527 | A1 | 6/2016 | McCullough | |
| 2018/0110922 | A1 * | 4/2018 | Dunki-Jacobs | A61J 1/2075 |

FOREIGN PATENT DOCUMENTS

| | | | | |
|---|---|---|---|---|
| JP | 2013500774 | A | 1/2013 | |
| JP | 2018509252 | A | 4/2018 | |
| WO | WO 2011/014525 | A2 | 2/2011 | |
| WO | WO-2014204894 | A2 * | 12/2014 | A61M 5/152 |
| WO | WO2016/0154413 | A1 | 9/2016 | |
| WO | WO2018/138022 | A1 | 8/2018 | |
| WO | WO 2018/165588 | A1 | 9/2018 | |
| WO | WO2019/079335 | A1 | 4/2019 | |

OTHER PUBLICATIONS

Notice of Reasons for Refusal and English-language machine translation, counterpart Japanese App. No. 2022-503982 (Dec. 5, 2023) (10 pages).

Extended European Search Report, counterpart EP App. No. 20844549.4 (Jul. 28, 2023) (11 pages).

* cited by examiner

MEDICAL FLUID INJECTION AND TRANSFER DEVICES AND METHOD

CLAIM OF PRIORITY

This application is the U.S. National Stage of PCT International Patent Application No. PCT/US2020/043515, filed Jul. 24, 2020, which claims priority to and the benefit of U.S. Provisional Patent Application No. 62/878,111, filed Jul. 24, 2019, the contents of which are hereby incorporated by reference in their entirety.

FIELD OF THE INVENTION

The present disclosure relates generally to devices for injecting medical fluids into patients and transfer devices for transferring medical fluids from containers and, in particular, to a medical fluid injection device or transfer device that uses inflation of a balloon within a container of the medical fluid to increase the pressure within the container to drive the medical fluid out of the container for injection or transfer.

BACKGROUND

Vials are one of the preferred container closure systems used by the pharmaceutical industry due to their extensive clinical history and record of long-term stability with a wide variety of drugs. Pharmaceutical drugs including biologics are often first commercially introduced in standard containers such as vials. Additionally, the industry has made a significant investment in capital equipment for aseptic vial filling. In normal use, vials typically require the transfer of the contained drug from the vial to another instrument such as a syringe and needle or injection device for delivery to the patient. New container closure systems such as prefilled syringes and cartridges have been introduced that allow direct transfer of the drug from the syringe or cartridge to the patient. Injection devices such as auto-injection devices and pens have been developed to utilize these newer forms of container closure. Because of uncertainty about long-term drug stability, and the extensive manufacturing resources already in place, devices that incorporate standard container closure systems such as vials, prefilled syringes or cartridges are greatly preferred by the pharmaceutical industry over devices that require a custom form of drug containment.

Typical syringes and auto-injection devices are limited on the viscosities of drug that can be delivered as well as by the forces that can be applied to the glass container closure systems. New injection devices have been developed including pumps for the delivery of insulin that use custom container closures, but these systems are very expensive, cannot generate high forces or pressures and typically are reusable and/or refillable.

Due to factors including stability and time to market, pharmaceutical drugs including biologics are often initially marketed in a lyophilized or powder form or in concentrated liquid form. Such drugs packaged in vials in both liquid and powder formulations can require significant preparation prior to administration. To facilitate the administration of liquid formulations in vials, drugs in vials are often packaged with an empty syringe and multiple needles for aspiration out of the vials and injection into the patient. In the case of powder formulations, an additional diluent or solution vial may be provided to allow for reconstituting the powder drug into solution available for injection. The risks associated with the preparation and administration of these drug forms is significant. They include the potential for needle stick injury during the reconstitution and administration process as well as errors with improper mixing and inaccurate dose volume or concentration delivered. This presents a real challenge for both trained caregivers and patients preparing and receiving the medication.

Similar issues of risk can also apply to the transfer of ready-to-inject drug that must be transferred from a vial to an injection device. This transfer involves removal of the drug from the vial, measurement of the proper dose, and injection into the patient using a syringe. Incomplete transfer of the full volume of the vial necessitates overfilling of the vial by some 25-30% and the associated waste. Contamination of the drug with non-sterile ambient air that is injected into the vial, or improper sterile technique can cause contamination of the injectable drug.

To overcome the abovementioned preparation and administration challenges with utilizing vials, new injection devices have been developed to allow for manual and/or automatic transfer of drug from the vial to a separate injection device at the point of use by the user. However, this can present challenges to the user including extra use steps and associated risk of errors as well as extra device materials to dispose of. This may ultimately affect the compliance of the therapy.

Accordingly, there continues to exist a need for new and/or improved apparatus and methods for injection of drugs from a source vial or vials to a subject and for otherwise transferring drugs from a source vial or vials.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, an injection device features a vial holder configured to hold a vial containing a medical fluid, a canister holder configured to hold a compressed gas canister and a balloon. A balloon spike is in fluid communication with the balloon and is configured to be inserted into a vial positioned in the vial holder and to selectively communicate with a compressed gas canister positioned within the canister holder so that the balloon is inflated within the vial to pressurize medical fluid within the vial. An injection spike is configured to be inserted into a vial positioned in the vial holder. An injection cannula is selectively in fluid communication with the injection spike so that medical fluid pressurized in the vial by inflation of the balloon flows through the injection cannula.

In another aspect, a transfer device for transferring medical fluid from a vial features a vial holder configured to hold a vial containing a medical fluid, a canister holder configured to hold a compressed gas canister and a balloon. A balloon spike is in fluid communication with the balloon and is configured to be inserted into a vial positioned in the vial holder and to selectively communicate with a compressed gas canister positioned within the canister holder so that the balloon is inflated within the vial to pressurize medical fluid within the vial. An injection spike is configured to be inserted into a vial positioned in the vial holder. A transfer conduit cannula is selectively in fluid communication with the injection spike so that medical fluid pressurized in the vial by inflation of the balloon flows through the transfer conduit.

In still another aspect, a process for transferring a medical fluid from a vial containing the medical fluid includes the steps of inserting a balloon spike into the vial, inserting an injection spike into the vial, inserting a balloon into the vial, inflating the balloon in the vial so as to increase a pressure of the medical fluid in the vial and transferring the pressurized medical fluid out of the vial through the injection spike.

BRIEF DESCRIPTION OF THE DRAWINGS

Examples of the subject matter of this patent application are shown for purposes of illustration only, and not limitation, in the attached drawings, of which.

DETAILED DESCRIPTION OF EMBODIMENTS

Embodiments of the disclosure relate to devices and methods for administering or transferring the contents of vials or other containers. The contents of the vial(s) or container(s) may be any suitable injectable, and for purposes of this description and claims, "injectable" includes without limitation drugs of any type, therapeutic or diagnostic, antibiotics, biologics, sedatives, sterile water and other injectable materials, either alone or in combination with one or more other injectables, and whether or not requiring reconstitution or concentration adjustment or other processing before injection.

The description below is for purposes of illustration only and not limitation. The present subject matter may be employed in a variety of apparatus, systems and methods not depicted below.

Embodiments of the disclosure may include an injection device or a transfer device with a compressed gas canister, a vial with stopper filled with injectable, a dual lumen vial spike or dual vial spikes, an expandable balloon, injection cannula or transfer conduit and an actuation button. The gas canister is in fluid communication with the balloon through the inlet side of the dual lumen vial spike or dual vial spikes. The balloon is initially collapsed and positioned within the inlet side of the dual lumen spike or dual vial spikes to allow for the spike(s) to easily pierce a rubber stopper. The outlet side of the dual lumen spike or dual vial spikes allows for fluid communication between the contents of the vial and an injection cannula or other device via a transfer conduit. In the case of an injection device, the injection button may be mechanically coupled to the injection cannula moveable within the device. In the case of a transfer device, the transfer conduit may be configured to deliver the medical fluid to the fill port of an injection device, such as the one disclosed in commonly assigned U.S. Pat. No. 9,925,333 to Hooven, et al., the contents of which are hereby incorporated by reference.

Figure 1:
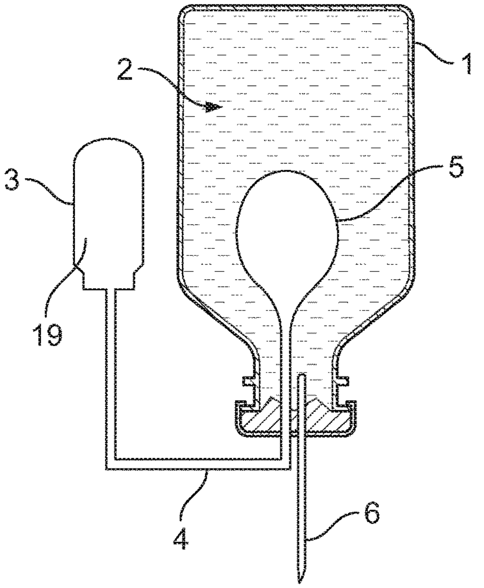
FIG. 1 is a schematic of a preloaded, single-vial injection system including an embodiment of the disclosure.

Embodiments of the disclosure may include a disposable one-time use injection device apparatus and method for administration into a subject such as a human being. For example, referring to FIG. 1, a general schematic illustrating a single-vial, preloaded or user-loaded injection system consisting of a vial 1 filled with injectable 2, a compressed gas canister 3, a balloon spike with an expandable balloon 5 and an injection cannula 6. The gas canister 3 is in fluid communication with the balloon 5 through a gas to balloon line 4 with a distal end that terminates in a balloon spike. The balloon is initially collapsed and positioned within the balloon spike to allow the spike to easily pierce a rubber stopper of the vial 1. The upper end of the injection cannula includes an injection spike that pierces the rubber stopper of the vial 1 as shown in FIG. 1 to allow for fluid communication between the contents 2 of the vial 1 and the injection cannula 6. In an alternative embodiment, the balloon spike and the injection spike may be incorporated into a single dual lumen spike with the inner lumen housing the balloon prior to inflation within the vial.

The injection system of FIG. 1 may be positioned within a housing that is provided with adhesive to attach the injection device to a patient or subject. An example of such an injection device is provided in commonly assigned PCT International Patent Application No. PCT/US2018/055624, International Publication No. WO 2019/075337, to Bourelle et al., the contents of which are hereby incorporated by reference.

Once the injection device is attached to the subject using the adhesive, the injection device button is activated. Activation of the button causes insertion of the balloon and injection spikes (or dual lumen spike) into the rubber stopper of the vial, puncture of the gas canister and insertion of the injection cannula into the subject. Compressed gas exits the canister to fill the balloon that is positioned within the vial. As the balloon expands within the rigid vial, the increase in pressure urges the injectable through the injection spike (or the outlet side of the dual lumen spike) into and through the injection cannula into the subject. The balloon may be designed to fill the internal space of the vial to sufficiently drive all of the medical fluid out to minimize residual. The balloon is be preferably configured to expand against the most distal wall and work itself toward the stopper end of the vial to ensure no trapped fluid. Orientation of the vial is not critical. Once all of the injectable is dispensed from the vial, the button is released and allows for automatic retraction of the needle. The injection device can be removed from the patient and discarded Insertion of the balloon and injection spikes (or dual lumen spike) into the rubber stopper may be difficult to the user if the diameter of the spike is large. In some embodiments, as described below, actuation of the button releases gas from the canister that aids the movement of the injection spikes or dual lumen spike into and through the stopper of the vial. Once the injection spikes or dual lumen spike is sufficiently inside the vial, the compressed gas starts to fill the balloon.

Figure 2:
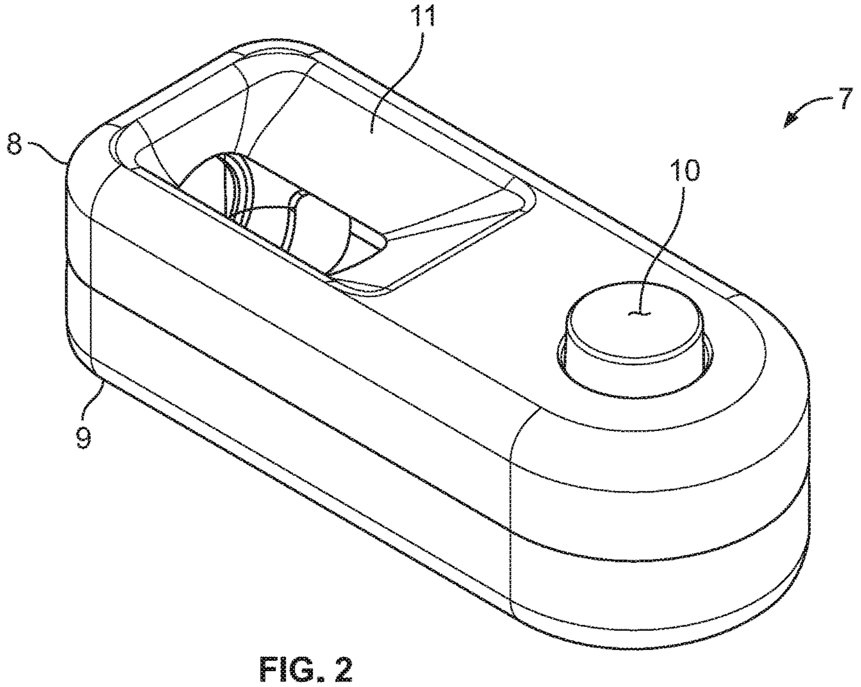
FIG. 2 is a perspective view of a single-vial injection device in an embodiment of the disclosure.

Referring to FIG. 2, an embodiment of a single-vial, preloaded injection device 7 includes an upper housing 8 and a lower 9 housing, an injection device or actuation button 10 and a viewing window 11 with the upper housing 8 to allow or visualization of a vial 1 positioned within a vial holder 40 (FIG. 3) therein, the contents of the vial 2 and the balloon 5. This viewing window 11 could also serve as an indicator of status of the injection device 7 during dispensing.

In an alternative embodiment, the injection device may not be preloaded with a vial. In other words, the upper housing 8 is removably secured to the lower housing 9 so that a vial may be positioned within the vial holder 40 by the user.

Figure 3:
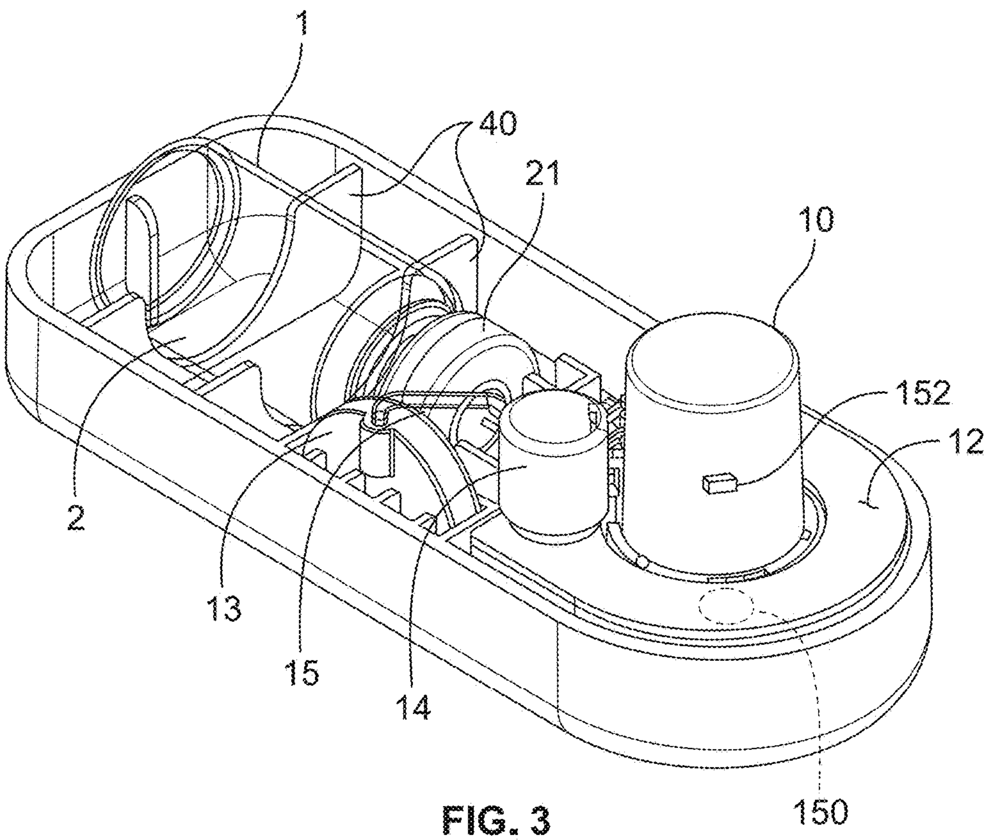
FIG. 3 is a perspective view of the single-vial injection device of FIG. 2 with the top cover removed to allow visualization of internal components.
Figure 4:
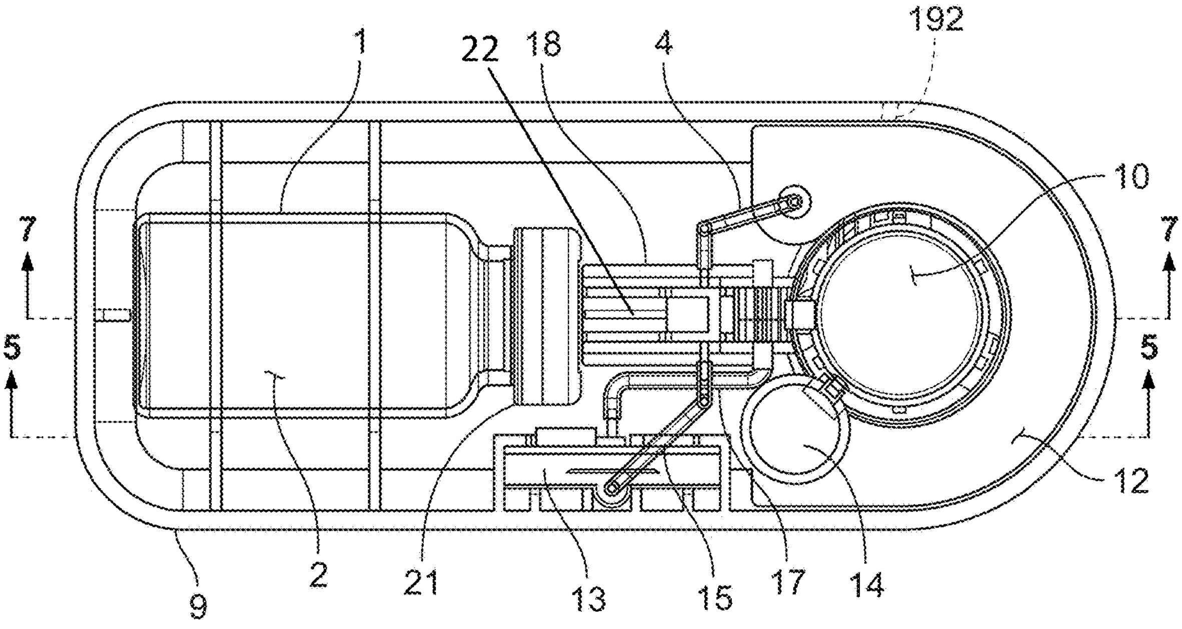
FIG. 4 is a top plan view of the injection device of FIG. 3.

Referring to FIGS. 3 and 4, the injection device of FIG. 2 is illustrated with the upper housing 8 removed. The components visible in this view include the lower housing 9, vial 1 with injectable 2, vial stopper or cap 21, canister cap 14, button 10, expansion chamber 12, gas to balloon line 4, vial spike holder 18, vial to filter line 15, filter 13, filter to cannula line 17.

Figure 5:
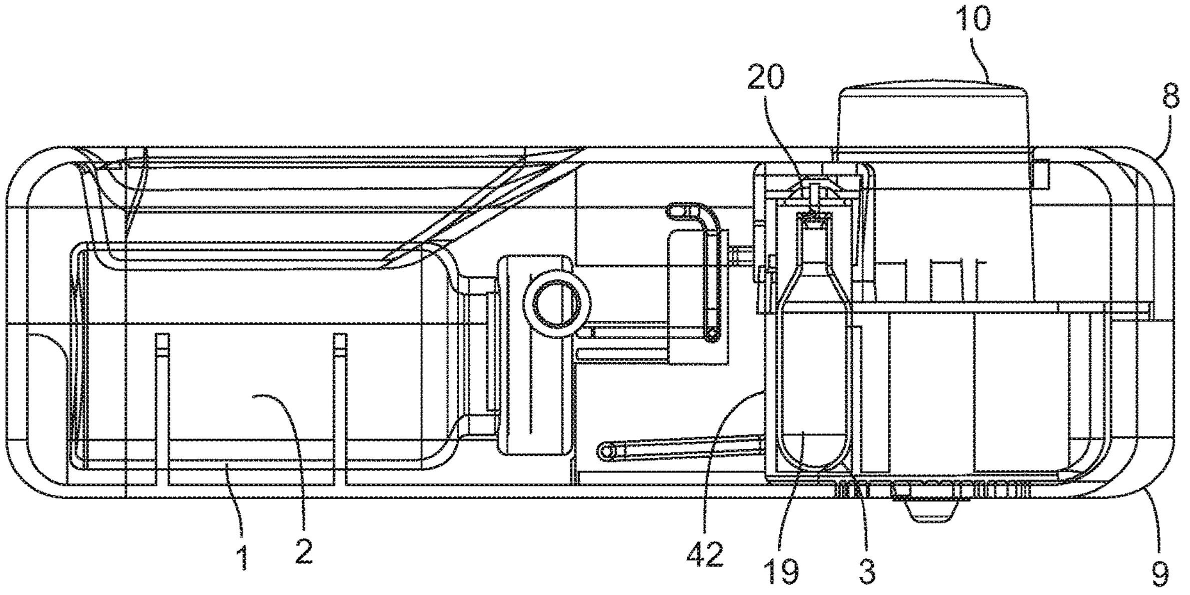
FIG. 5 is a cross-sectional view taken along line 5-5 of FIG. 4 illustrating the compressed gas canister before the injection device button is pushed.
Figure 7:
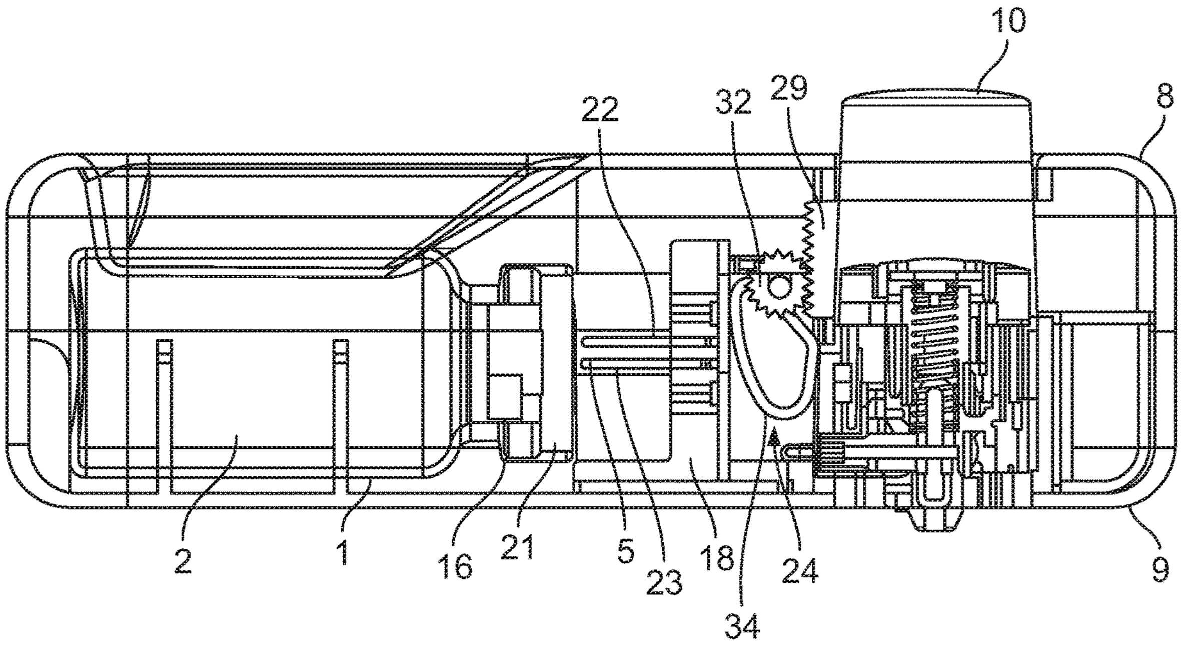
FIG. 7 is a cross-sectional view taken along line 7-7 of FIG. 4 illustrating the holder driver before the injection device button is pushed.

Referring to FIGS. 5 and 7, the injection device of FIGS. 2-5 is shown in the pre-fire state. The compressed gas canister 3 is positioned within a canister holder 42 (FIG. 5) and sealed within the expansion chamber 12 with a canister cap 14. In an alternative embodiment, where the device is reusable, the canister cap 14 may be removable also so that compressed gas canister 3 may be replaced after use.

The canister cap 14 and a canister spike 20 move with the button 10. The button also interacts with a holder driver, indicated in general at 24 in FIGS. 7 and 8. The holder driver 24 includes the dual vial spikes including injection spike 22 and the balloon spike 23 with included balloon 5 in a deflated state. As noted previously, in an alternative embodiment, a single dual lumen vial spike may be substituted for the dual vial spikes.

Figure 8:
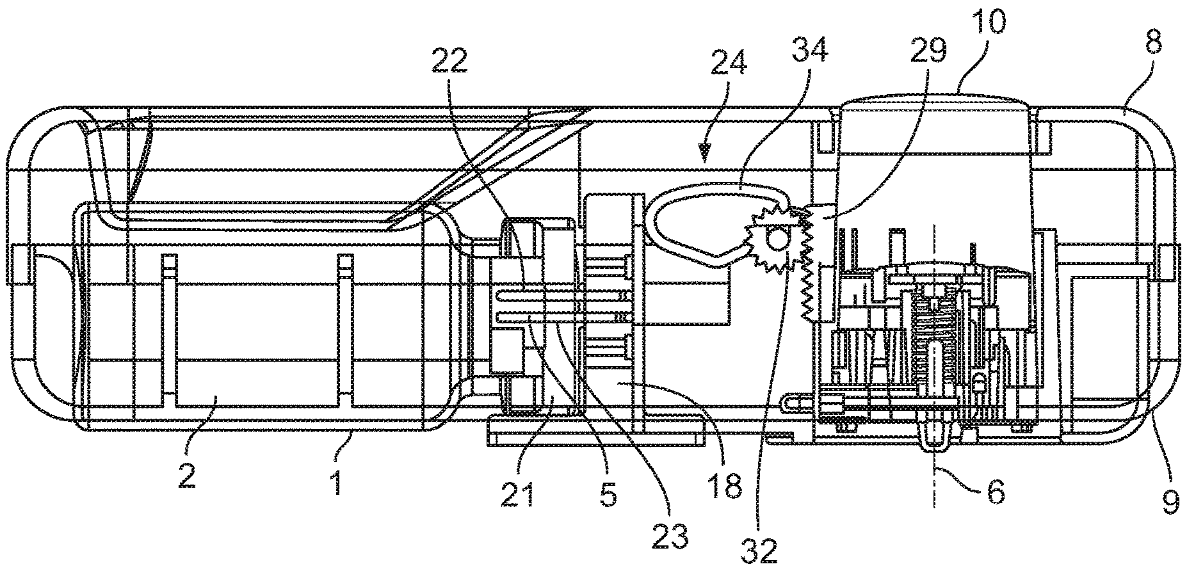
FIG. 8 shows the injection device of FIG. 7 after the injection device button is pushed and the drug vial is pierced.

With reference to FIGS. 7 and 8, in the illustrated embodiment, the holder driver 24 includes a gear rack 29 that is attached to the button 10 so as to move with the button. In addition, the holder driver 24 includes a gear 32 rotatably mounted within the lower housing that is engaged and rotated by the gear rack 29 as the button 10 is pressed and depressed. A cam 34 is secured to the gear 32 in a fixed fashion so at to move between the positions illustrated in FIGS. 7 and 8 as the gear is rotated via actuation of the button 10. As the cam 34 moves from the position shown in FIG. 7 into the position shown in FIG. 8, it engages the vial spike holder 18, which is slidably positioned within the lower housing. The injection spike 22 and the balloon spike 23 pierce the vial stopper 21 as the spike holder 18 slides into the position illustrated in FIG. 8 due to the urging of cam 34.

Figure 6:
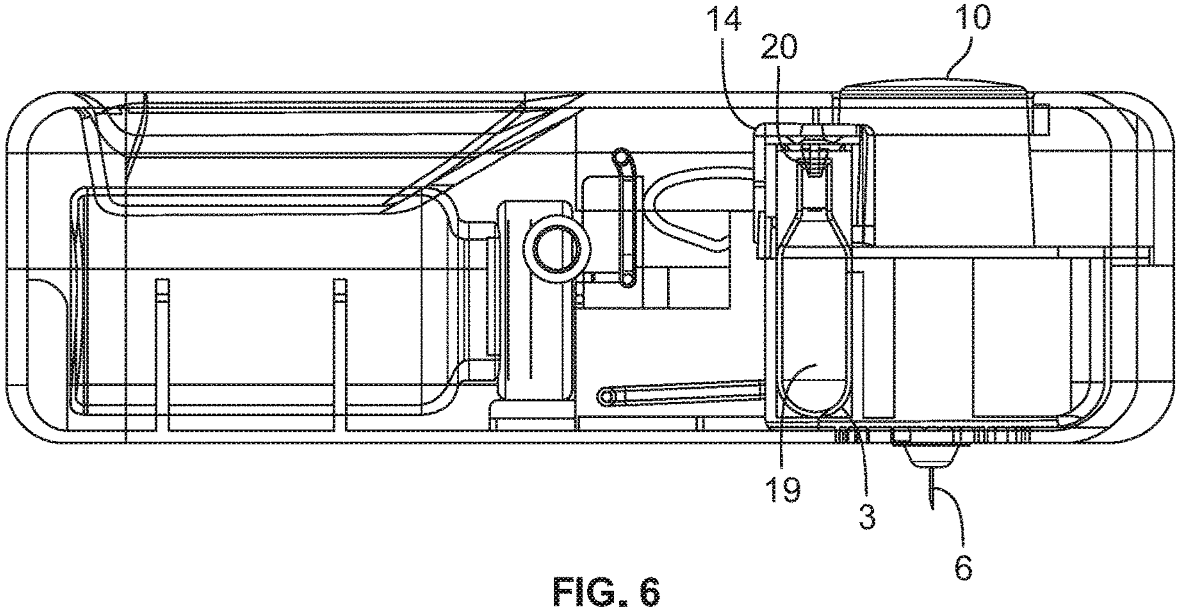
FIG. 6 shows the injection device of FIG. 5 illustrating the compressed gas canister after the injection device button is pushed.

Referring to FIGS. 6 and 8, once the button 10 in pushed, the cannula 6, which is coupled to the button 10, is extended from the lower housing (as illustrated in FIG. 8). As an example only, an arrangement for coupling the button 10 to the cannula is provided in commonly assigned U.S. Pat. No. 9,925,333 to Hooven, et al., the contents of which, as noted above, are hereby incorporated by reference.

Figure 13A:
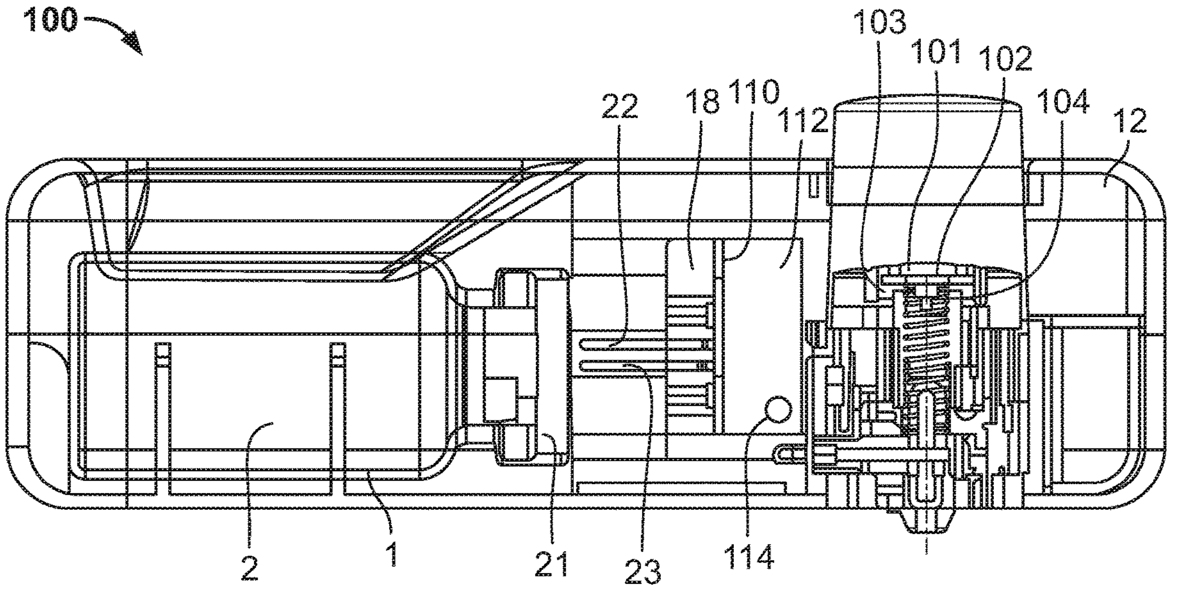
FIG. 13A is a cross-sectional view illustrating the holder driver in a second embodiment of the disclosure before the injection device button is pushed.
Figure 13B:
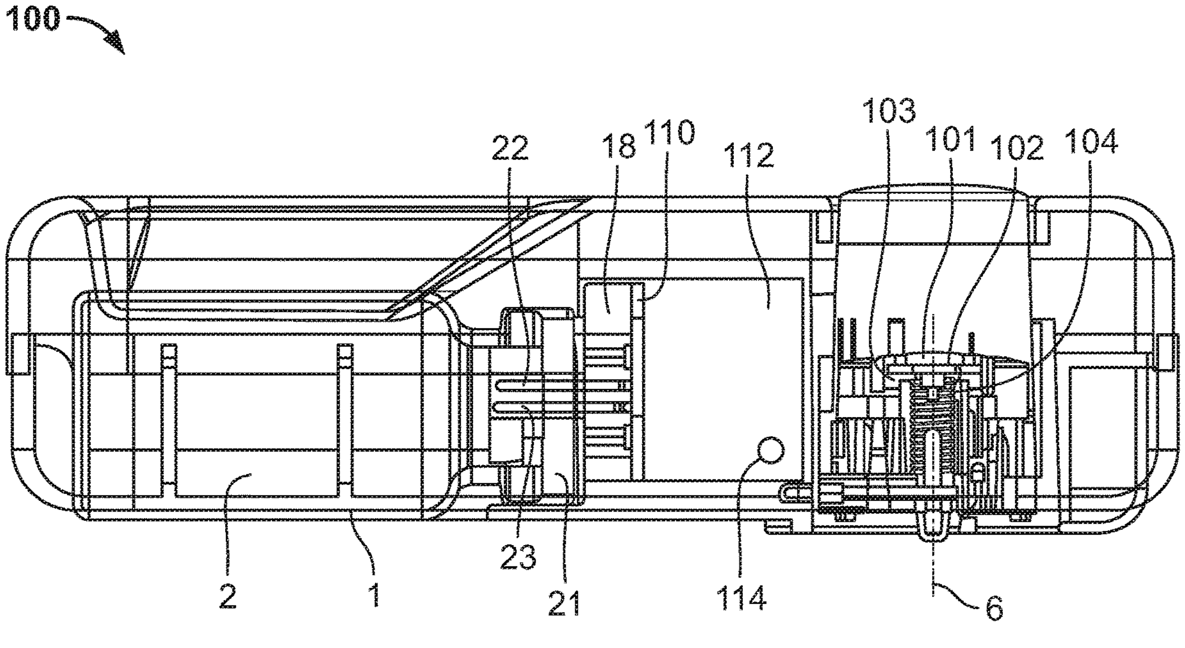
FIG. 13B shows the injection device of FIG. 13A after the injection device button is pushed and the drug vial is pierced.

An alternative embodiment of the injection device is indicated in general at 100 in FIGS. 13A and 13B, where components shared with the previous embodiments use the same reference numbers. The injection device of FIGS. 13A and 13B functions in the same manner as the previous embodiments with the exceptions described with reference to FIGS. 13A-22C.

In the injection device 100 of FIGS. 13A and 13B, to aid the movement of the injection cannula 6, compressed gas from the expansion chamber 12 is optionally directed via a line or port to a cylinder 101 so as to move a cannula piston 102, connected to a spring-loaded cannula holder 104, to urge the cannula into the extended position (shown in FIG. 13B). The compressed gas translates the cannula piston 102 into a relief 103 (also shown by arrow 105 in the schematic of FIG. 14), which allows for the cannula piston to stop translating and allowing the gas to flow around the piston into a cylinder 112 to insert spike(s) into the vial and then to the balloon spike 23 (FIGS. 7 and 8) to start the inflation of the balloon. In such an embodiment, the button 10 may still be connected to the injection cannula 6 so that the gas pressure assists the user in deploying the injection cannula, or the button 10 may be disconnected from the injection cannula 6 and the gas pressure may provide the entire force necessary to deploy the injection cannula. The cannula holder 104 could also serve as a valve to allow the gas to proceed to the balloon in the vial only after the injection cannula is in the dispense position illustrated in FIG. 13B.

The button 10 is also coupled to the canister cap 14 and urges the cap towards the canister 3 when the button is pressed allowing the canister spike 20 to puncture the canister 3 to allow the flow of compressed gas 19 to fill the expansion chamber 12. As an example only, the pressure in the gas canister 3 can range from 500 to 4000 psi. The gas 19 is preferably nitrogen as many drugs are sensitive to oxidation from air so nitrogen is used because it is inert. Once the gas 19 fills the expansion chamber 12, the pressure within this 12 is reduced to approximately 50 psi (as an example only). The purpose of the expansion chamber 12 is to reduce the pressure of gas into a larger volume as a safety to not risk bursting the vial 1.

In alternative embodiments, the expansion chamber 12 may be replaced by an alternative pressure regulation device, many of which are known in the prior art.

As described above, the button 10 also interacts with the holder driver 24 to insert the injection spike 22 and balloon spike 23 through the vial stopper 21 to access the internal contents 2 of the vial 1.

An alternative embodiment of the injection device 100 of FIGS. 13A and 13B, uses compressed gas to aid the movement of the injection spike 22 and balloon spike 23 through the vial stopper 21 to access the internal contents 2 of the vial 1. More specifically, compressed gas from the expansion chamber 12 moves a spike piston 110 connected to vial spike holder 18 to urge the spikes 22 and 23 (or a dual lumen spike) from the position shown in FIG. 13A to the position shown in FIG. 13B so that the spike(s) pass through the vial stopper 21. The spike piston is slidably positioned within a cylinder 112 that receives compressed gas from the expansion chamber 12 via the injection cannula driving piston relief 103 (FIGS. 13A and 13B) and a port 114. The port 114 may be in direct communication with the relief 103 or may communicate with the relief 103 via a gas line (not shown). In embodiments where pressurized gas does not assist in extending the injection cannula 6, and thus there is no cylinder 101, no cannula piston 102 and no relief 103 of FIGS. 13A and 13B, the port may receive pressurized gas directly from expansion chamber 12 or through a gas line extending between the expansion chamber 12 and the port 114.

Figure 14:
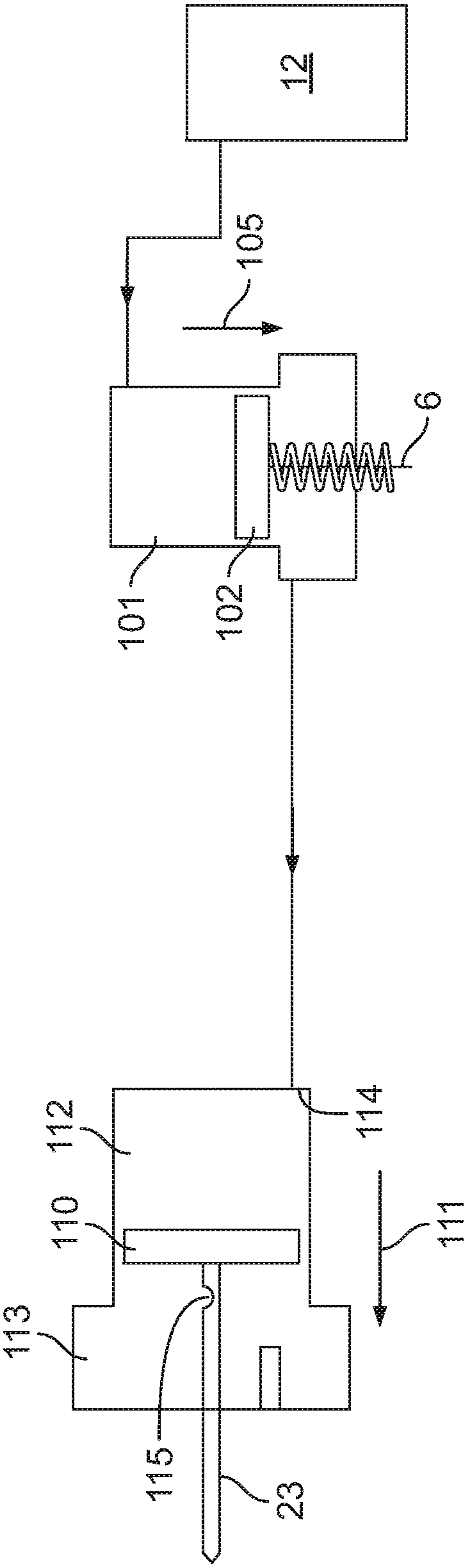
FIG. 14 is a schematic of an alternative embodiment of the disclosure.

In another alternative embodiment, a schematic of which is illustrated in FIG. 14, the compressed gas may translate the spike piston 110 in the direction of arrow 111 into a relief 113, which allows for the piston to stop translating and allows the gas to flow around the piston into a side aperture 115 in the balloon spike 23 to start the translation of the wrapped balloon into the vial and inflation of the balloon.

Figure 9:
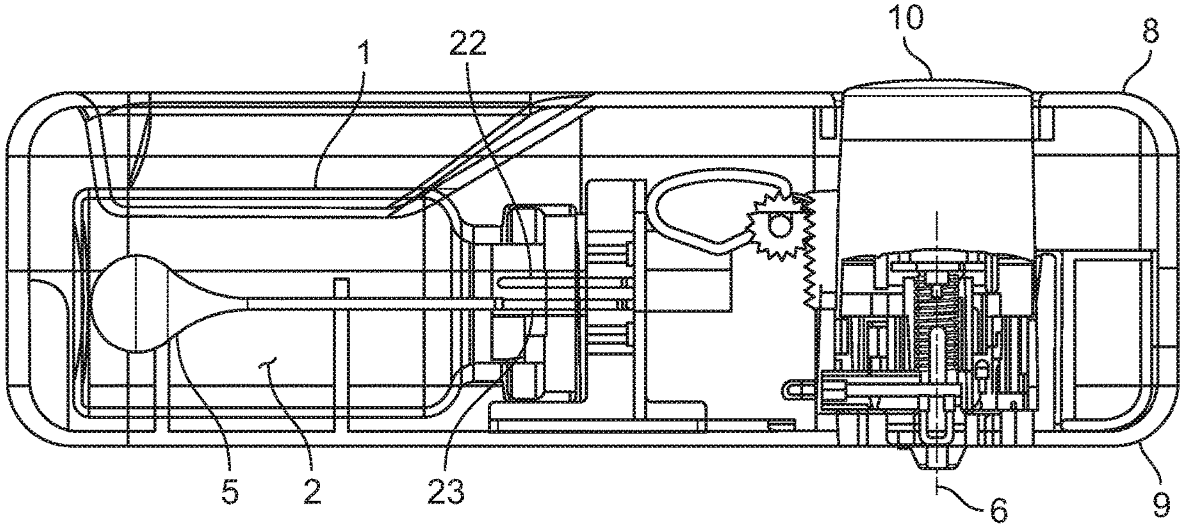
FIG. 9 shows the injection device of FIG. 8 after filling of the balloon and dispensing of the drug has been initiated.

Referring to FIGS. 4 and 9, after the distal end portions of the spike(s) are positioned within the vial, gas 19 within the expansion chamber 12 travels through the gas to balloon line 4 into the balloon spike 23. The gas 19 urges the balloon 5 out of the balloon spike 23 towards the back of the vial 1 and starts initial inflation. The balloon 5 is designed to unwrap out of the balloon spike 23 towards the back of the vial 1. An example of an arrangement for storing the collapsed balloon 5 within the lumen of the balloon spike 23 as the balloon spike pierces the vial stopper, and then deploying and inflating the balloon after positioning within the vial, is provided in U.S. Pat. No. 7,883,499 to Fangrow, the contents of which are hereby incorporated by reference. Alternatively, as described below, the balloon may be extended and wrapped on a mandrel positioned within the balloon spike. Manufacturing of the balloon may employ various dipping techniques to achieve the correct dimensions before and after inflation. Examples of suitable materials for the balloon are provided in commonly assigned U.S. Patent Application Publication No. US 2015/0217058 to Hooven, et al., the contents of which are hereby incorporated by reference.

Figure 15A:
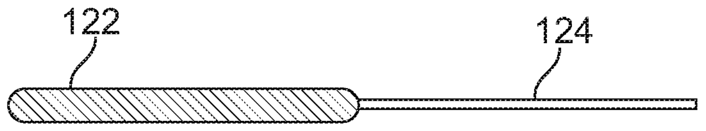
FIG. 15A shows a balloon and mandrel in the second embodiment of the disclosure with the balloon in the deflated and wrapped configuration.
Figure 15B:
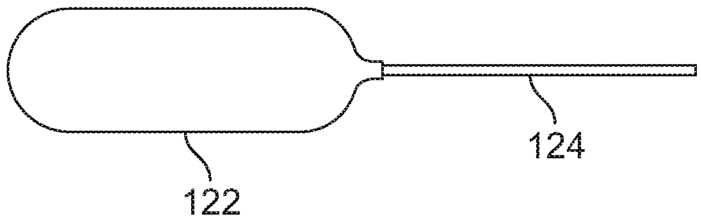
FIG. 15B shows the balloon and mandrel of FIG. 15A with the balloon in the inflated configuration
Figure 16A:
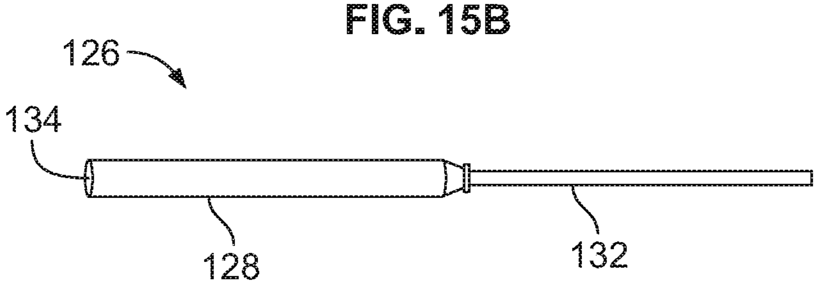
FIG. 16A shows a holding tube in the second embodiment of the disclosure.
Figure 16B:
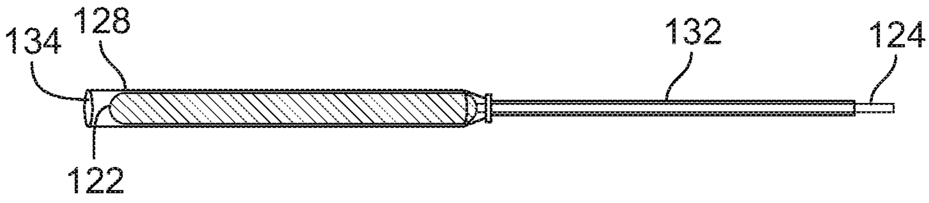
FIG. 16B shows the balloon and mandrel of FIG. 15A positioned within the holding tube of FIG. 16A.
Figure 17:
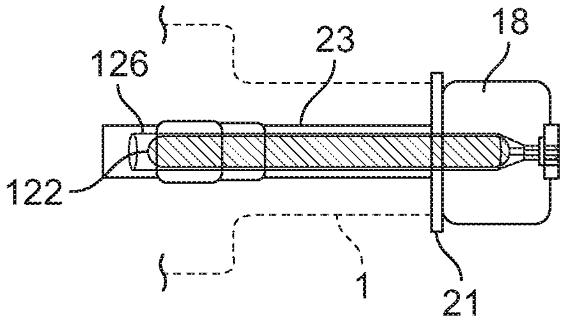
FIG. 17 shows the holding tube, balloon and mandrel of FIG. 16 positioned within a spike after insertion of the spike into a vial.

An alternative embodiment of the arrangement for storing the collapsed balloon within the lumen of the balloon spike for piercing the vial stopper, and then deploying and inflating the balloon, will now be described with reference to FIGS. 15A-18C. As illustrated in FIG. 15A, a balloon 122 is in a wrapped or furled configuration and positioned upon the distal end of an inflation tube or mandrel 124. A balloon holding tube, indicated in general at 126 in FIG. 16A, includes an enlarged balloon storage portion 128 and a mandrel or inflation tube receiving portion 132 that, as illustrated in FIG. 16B, receive the wrapped or furled balloon 122 and the mandrel or inflation tube 124, respectively. The balloon storage portion 128 of the holding tube 126 features an open distal end 134. As illustrated in FIG. 17, the holding tube containing the wrapped or furled balloon and inflation tube or mandrel (of FIG. 16B) is positioned within the balloon spike 23. When in this configuration, the balloon spike is inserted through a vial stopper 21 and into a vial (indicated in phantom at 1 in FIG. 17).

Figure 18A:
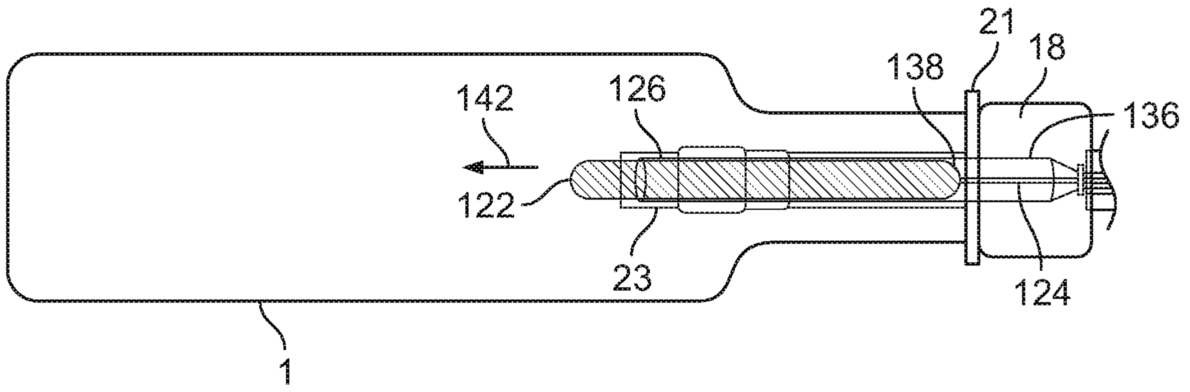
FIG. 18A shows the spike, holding tube, balloon and mandrel of FIG. 17 as the balloon begins exiting the holding tube and the spike.
Figure 18B:
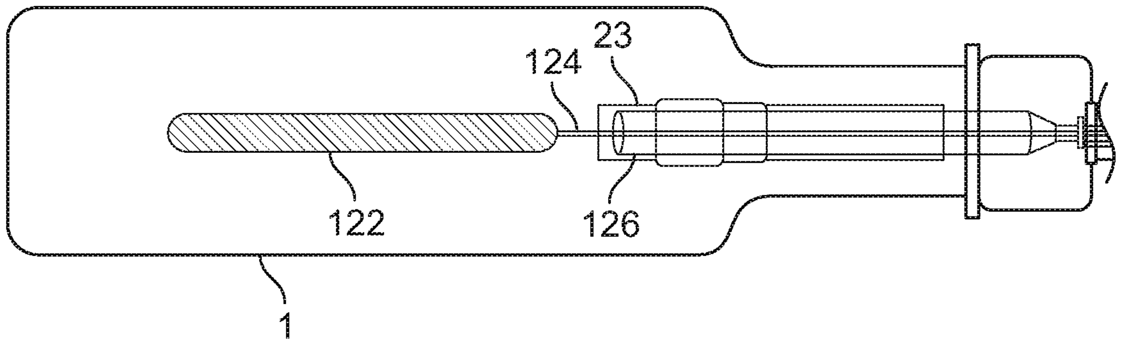
FIG. 18B shows the spike, holding tube, balloon and mandrel of FIG. 18A as the balloon completes exiting the holding tube and the spike
Figure 18C:
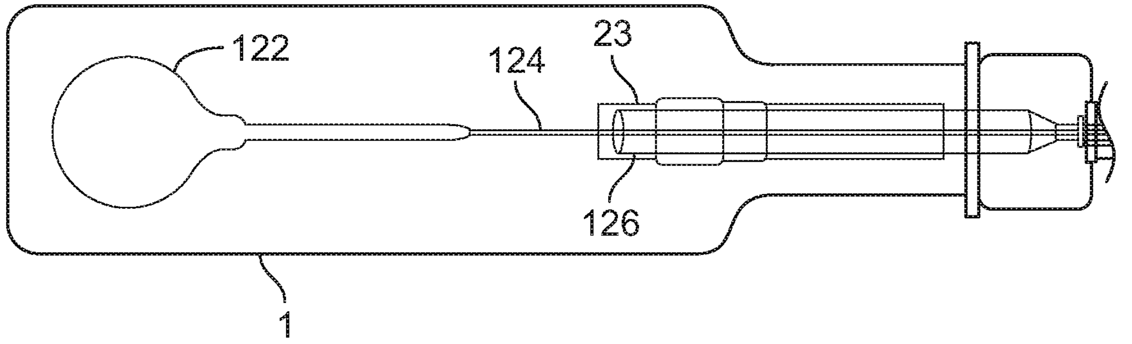
FIG. 18C shows the spike, holding tube, balloon and mandrel of FIG. 18B with the balloon partially inflated.

Deployment of the balloon 122 of FIG. 17 within the vial is illustrated in FIGS. 18A-18C. A gas passage 136 is formed within vial the spike holder 18 is in fluid communication with the cylinder 112 (FIGS. 13A and 13B) and, as a result, pressurized gas flows through the gas passage 136 and pushes on the proximal end (138 in FIG. 18A) of the balloon 122 so that the balloon in moved out of the holding tube 126 and balloon cannula 23 in the direction of arrow 142 of FIG. 18B and into the position illustrated in FIG. 18B. The balloon 122 then begins to inflate, as illustrated in FIG. 18C, due to pressurized gas (also from cylinder 112 of FIGS. 13A and 13B) flowing through the inflation tube 124. This continues until the balloon is fully inflated (as illustrated in FIG. 15B or in FIG. 12 for balloon 5).

The balloon 5 (or 122) is designed to fill the back of the vial 1 first then proceed forward. This can be done by having a thin section in the back and thicker towards the front of the vial 1. The advantage of this is to allow the balloon 5 to drive all of the injectable 2 out of the vial 1 regardless of vial 1 orientation.

Once the balloon 5 (or 122) starts to fill with gas 19, the increasing volume of the balloon urges injectable 2 out of the vial 1 through the injection spike 22. The injectable 2 is urged through the vial to filter line 15 through the filter 13. The filter 13 is comprised of hydrophilic and hydrophobic filter media. The drug 2 is allowed to flow through the hydrophilic but not the hydrophobic filter media. Any gas that was present in the vial commonly referred to as headspace that is expelled out of the vial during transfer or after all of the injectable is expelled is allowed to flow through the hydrophobic but not the hydrophilic filter media. This has the advantage of only delivering injectable 2 to the patent through the injection cannula 6 and not gas 19. An example of such a filtration arrangement is provided in commonly assigned PCT International Patent Application No. PCT/US2018/056130, International Publication No. WO 2019/079335, to Bourelle et al., the contents of which are hereby incorporated by reference.

Figure 10:
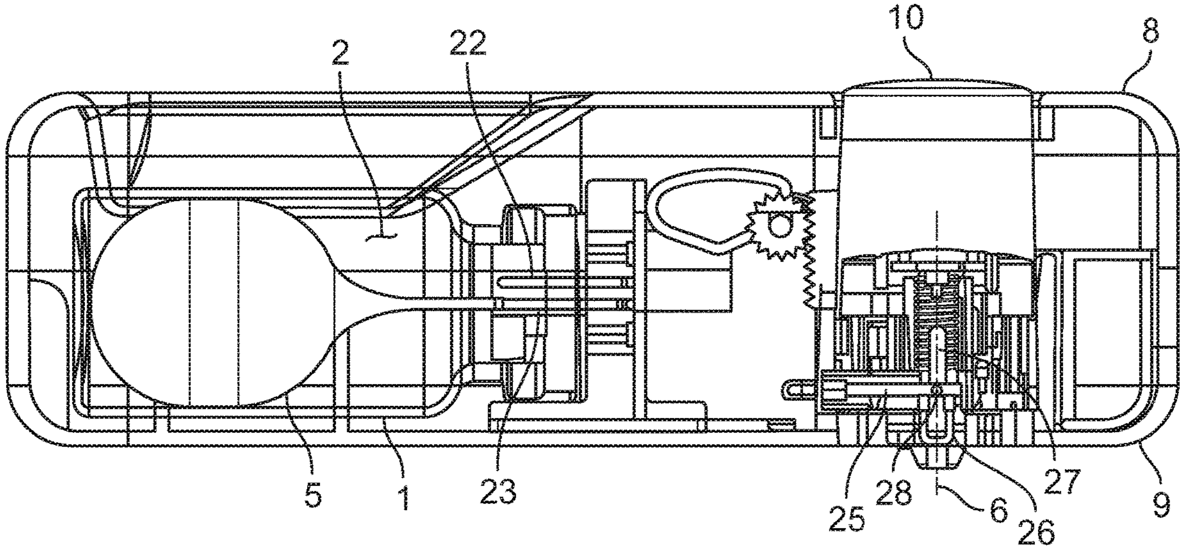
FIG. 10 shows the injection device of FIG. 9 during further filling of the balloon and dispensing of the drug.

Referring to FIGS. 4 and 10, the injectable 2 is urged through the filter 13, through the cannula line 17 into the cannula manifold 25. Within the cannula manifold 25 is the cannula 6. The cannula 6 is sealed with an upper 26 and lower 27 septum to seal around the outside of the cannula 6. A side hole 28 within the cannula 6 allows the injectable to flow from manifold 25 through the inner diameter of the cannula 6 into the patient. An example of such an arrangement is provided in commonly assigned U.S. Pat. No. 9,925,333 to Hooven, et al., the contents of which, as indicated above, are incorporated by reference.

With reference to FIG. 10, as more gas 19 fills the balloon 5 (or 122) within the vial 1, more injectable 2 is forced out of the vial 1 and into the patient.

Figure 11:
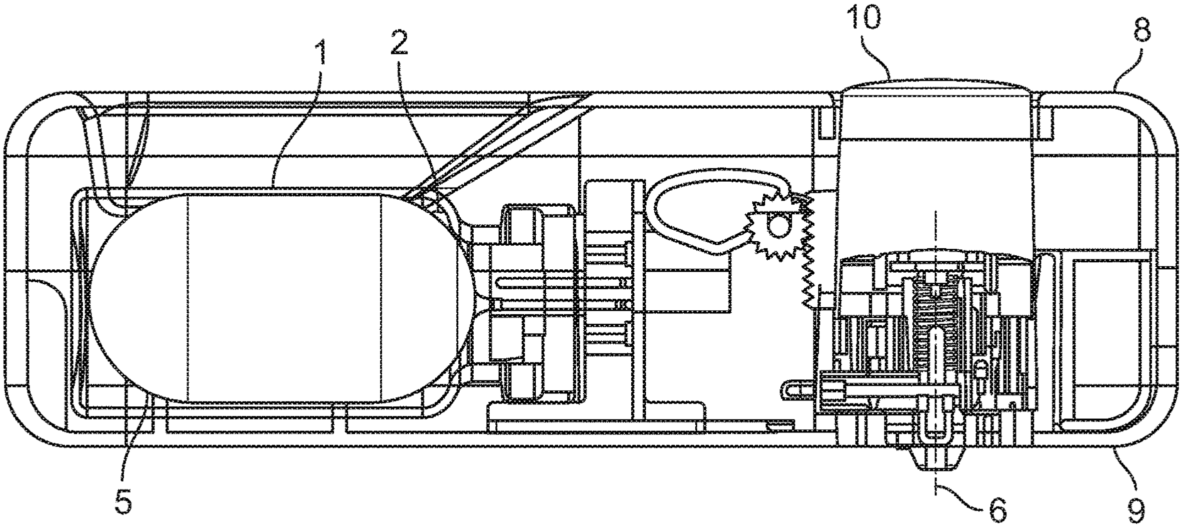
FIG. 11 shows the injection device of FIG. 10 at the end of drug dispensing with the balloon filled.

Referring to FIG. 11, the balloon 5 (or 122) is almost completely filled within the vial 1 to expel a majority of the injectable 2 out of the vial 1 and into the patient. As previously discussed, the preferred method of filling the balloon 5 is from the back of the vial 1 to the front to insure all of the injectable 2 is removed from the vial 1 to reduce the left-over residual of injectable 2 within the vial 1 as much as possible. The balloon may optionally be provided with axial grooves formed in the exterior surface, or the balloon provided with small axial thick sections, to create paths for fluid flow to minimize trapped fluid behind the balloon as it expands against the inner walls of the vial.

Figure 12:
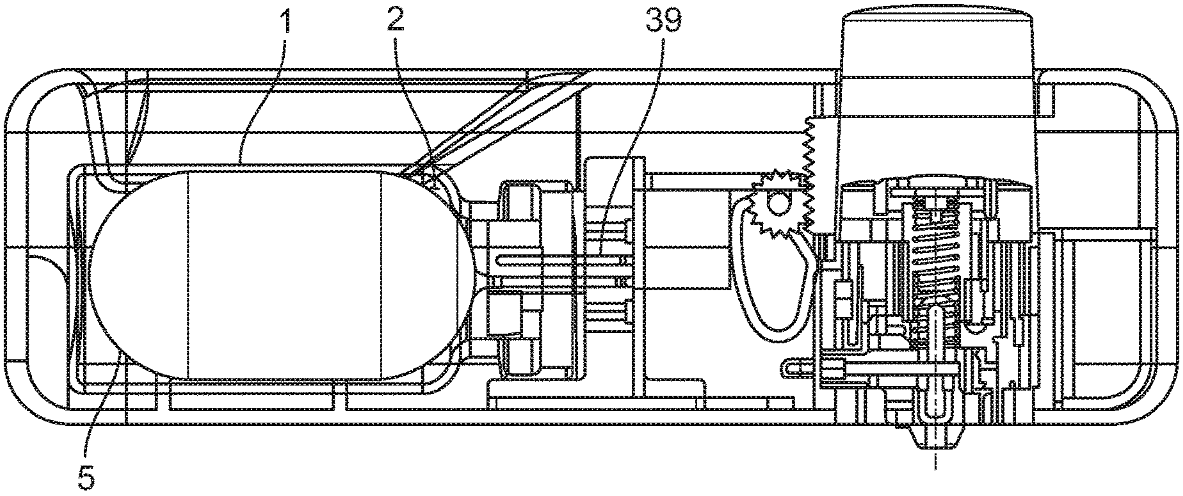
FIG. 12 shows the injection device of FIG. 11 after the end of drug dispensing with the button retracted into a lockout position

Referring to FIG. 12, once the balloon 5 (or 122) has filled the vial 1 nearly completely, and expelled a substantial amount of injectable 2 from the vial 1, the balloon triggers a button release mechanism 39. This allows the button 10 to raise and the cannula 6 to automatically retract and lockout reactivation of the injection device by the patient providing notification that the administration is complete.

As examples only, the button release mechanism may include a switch, button or other member that is engaged by the fully (or nearly fully) inflated balloon 5 and an associated linkage or other mechanism that activates the automatic needle/cannula retraction mechanism disclosed in commonly assigned U.S. Pat. No. 9,925,333 to Hooven, et al., the contents of which, as indicated above, are incorporated by reference. Alternatively, the button release mechanism 39 may be triggered, for example, by a decreased fluid flow rate through either the injection spike or the balloon spike or associated lines (or a combination thereof). As yet another example, the button release mechanism may be triggered by a change in gas pressure within the expansion chamber 12 (of FIG. 4).

The injection device may also include a vent valve that is in fluid communication with the lumen of the balloon spike and a venting port. The vent valve may be configured so as to be opened by the button release mechanism 29 after the completion of the dispensing/injection of the drug so that the pressurized gas within the balloon is vented outside of the injection device housing.

In an alternative embodiment, the expansion chamber 12 is provided with a vent valve assembly, indicated in phantom at 150 in FIG. 3. As explained below, the vent valve assembly engages a locking tab 152 formed on the button 10 after the button is pushed to initiate an injection. The vent valve assembly is activated upon pressurization of the expansion chamber 12 after the pressurized gas canister 19 (FIG. 5) is punctured. The button 10 stays in a lowered or retracted position until all of the medical fluid has transferred to the patient and the gas starts ventin. Once the pressure in the expansion chamber drops below a predetermined pressure, the vent valve assembly opens, allowing for the release of the button 10 to the raised or extended position illustrated in FIGS. 2 and 3.

Figure 19:
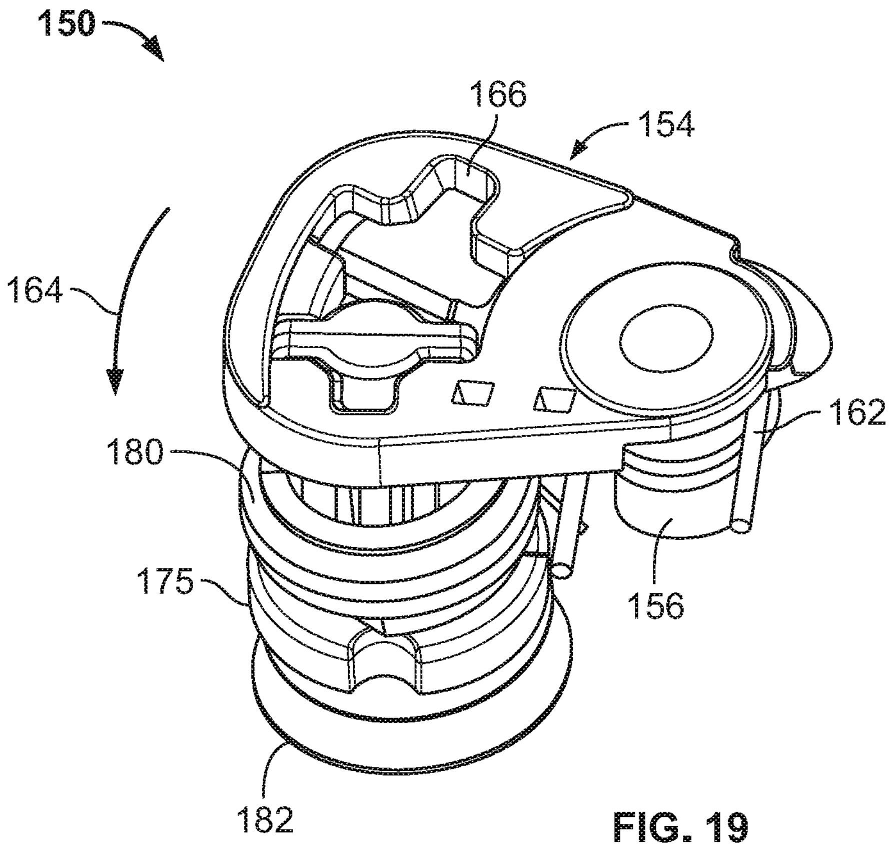
FIG. 19 is a perspective view of vent valve assembly in the second embodiment of the disclosure.
Figure 20:
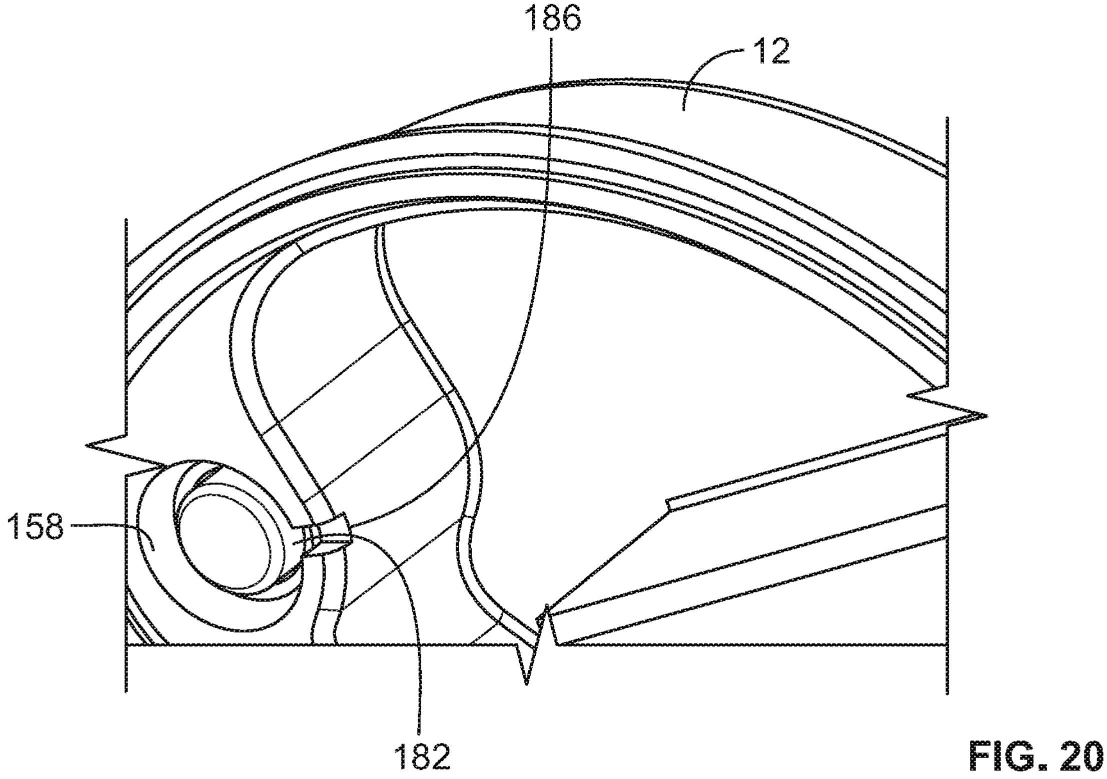
FIG. 20 is a bottom perspective partial view of the expansion chamber showing a vent port in the second embodiment of the disclosure.
Figure 21:
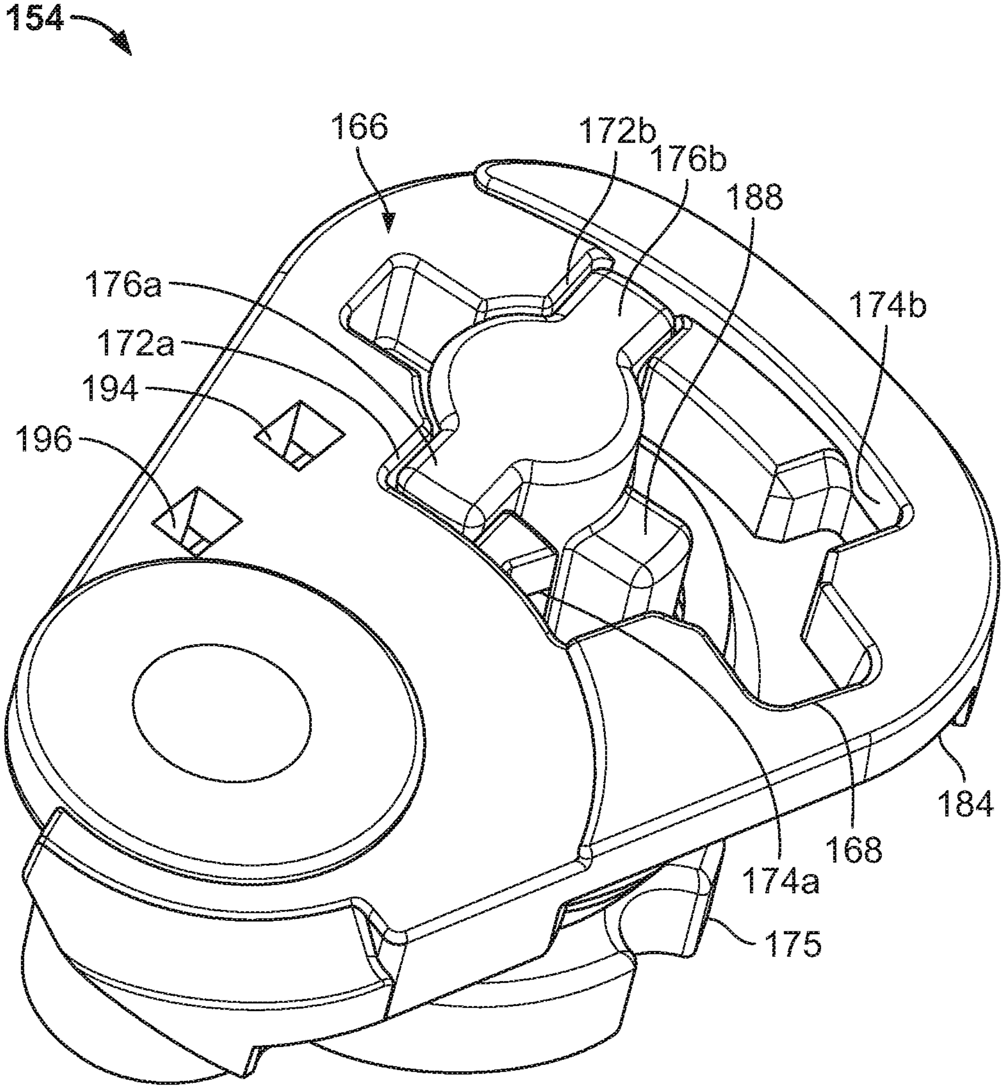
FIG. 21 is an enlarged view of the pivot plate and piston head of the vent valve assembly.

An embodiment of the vent valve assembly of FIG. 3 referenced above is indicated in general at 150 in FIG. 19. A pivot plate, indicated in general at 154, is pivotally attached to a mounting post 156 which is positioned on the exterior top surface of the expansion chamber 12 adjacent to a venting bore, illustrated at 158 in FIG. 20. A torsion spring 162 is also positioned upon the mounting post 156 and urges the pivot plate 154 to rotate in the counterclockwise direction (arrow 164). As shown in FIG. 19, the pivot plate includes an arcuate main slot 166. As shown in FIG. 21, the arcuate slot 166 of the pivot plate has a stop wall 168, an opposing pair of recesses **172*a* and 172*b* and an opposing pair of slots 174*a* and 174*b***.

As illustrated in FIGS. 19, 21 and 22A-22C, a pressure relief piston 175 is positioned within the venting bore 158 and the arcuate main slot 166 of the pivot link 154. The piston includes a piston head having arms **176*a* and 176*b*. As illustrated in FIG. 21, the arms 176*a* and 176*b* of the piston are initially positioned within the recesses 172*a* and 172*b* of the pivot plate 154 due to the downward urging (arrow 178 of FIG. 22A) of a compression coil spring 180 of FIGS. 19 and 22A-22C. As illustrated in FIGS. 20 and 22A-22C, the bottom of the pressure relief piston 175 is provided with an annular seal 182 that is positioned within and closes the venting bore 158 when the vent valve assembly 150 is in the configuration of FIGS. 20-22**A, which corresponds to the initial condition of the injection device before the pressurized gas cartridge is punctured.

After the user pushes the button 10 and moves it towards the retracted position illustrated in FIG. 13B (with the injection cannula 6 extended), and the gas canister is punctured, the push button locking tab 152 of FIG. 3 engages latching notch 184 (FIG. 21) of the pivot plate 154 so as to be latched in the downward or retracted position.

As described above, the act of pushing the button 10 causes the pressurized gas cartridge (19 of FIGS. 5 and 6) to be punctured, thus filling the pressurized gas expansion chamber 12 with pressurized gas. This pressure in the gas expansion chamber pushes on the bottom of the annular seal 182 which forces the pressure relief piston 175 to raise into the position illustrated in FIG. 22B against the urging of the compression spring 180. As a result, with reference to FIG. 22B, the arms **176*a* and 176*b* of the piston head rise up out of the recesses 172*a* and 172*b* (FIG. 21) of the pivot plate 154. The pivot plate 154 then rotates due to the urging of the torsion spring 162 in the direction of arrow 164 of FIG. 19 until a piston stop 188 (FIG. 21) of the pressure relief piston 175 contacts the stop wall 168 (FIG. 21) of the pivot plate 154. At this point, the annular seal 182 is still positioned within the venting bore 158 and the venting bore remains closed as the injection is performed. The tab 152 (FIG. 3) of the button remains latched by the pivot plate 154** so that the button remains in the lowered or retracted position.

As the injection is completed, the balloon expands to its fully inflated (or near fully inflated) condition. The sizing of the balloon 5 or 122 and the expansion chamber 12 may be such that the full (or near full) inflation of the balloon 5 or 122 causes a decrease of the pressure within the expansion chamber 12. Alternatively, or in addition, a venting port, illustrated in phantom at 192 in FIG. 4, may be formed in the expansion chamber and sized so as to permit slow venting of the expansion chamber 12 at rate that does not to interfere with the inflation of the balloon 5 or 122. As the pressure in the expansion chamber 12 slowly decreases, the compression spring 180 (FIGS. 19 and 22A-22C) begins to expand or extend and, with reference to FIGS. 22B and 22C, the annular seal 182 of the pressure relief piston 175 moves downwards within the venting bore 158. A venting notch, indicated at 186 in FIGS. 20 and 22A-22C, is formed in the expansion chamber 12. When the annular seal 182 drops below the notch, the compressed air from within the expansion chamber 12 bypasses the annular seal and enters the venting bore 158. This causes further movement of the annular seal 182 downwards into the expansion chamber so that the remaining pressurized air within the expansion chamber quickly vents through the venting bore 158 and out through venting ports 194 and 196 (FIG. 21) formed in the pivot plate 154 in a final venting stage.

Figure 22A:
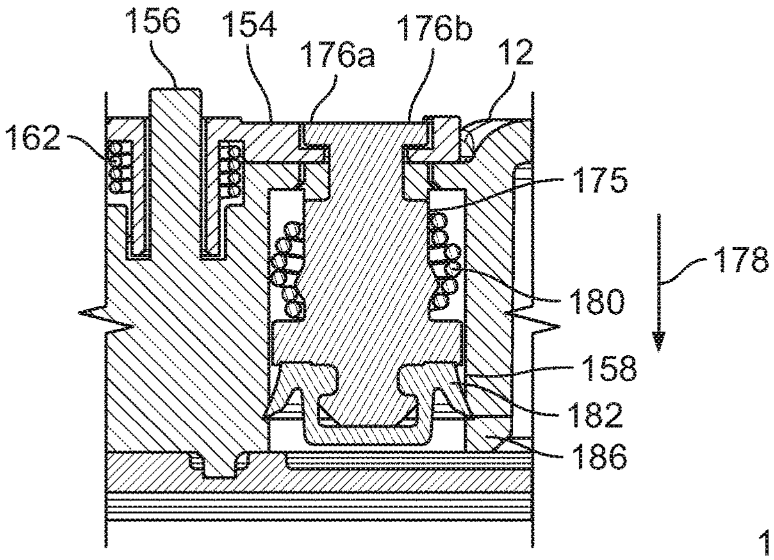
FIG. 22A is a cross-sectional view of the vent valve assembly and vent port of FIGS. 19-21 in an initial configuration prior to the injection device button being pushed.
Figure 22B:
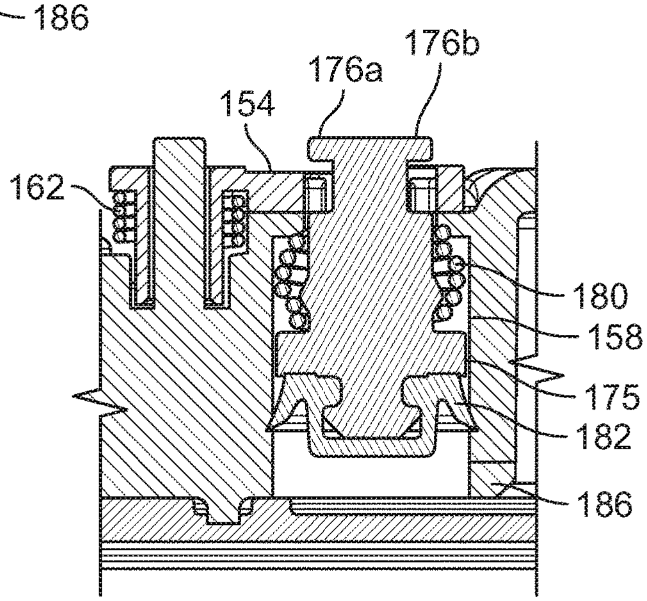
FIG. 22B is a cross-sectional view of the vent valve assembly and vent port of FIG. 22A in a pressurized configuration after the injection device button has been pushed.
Figure 22C:
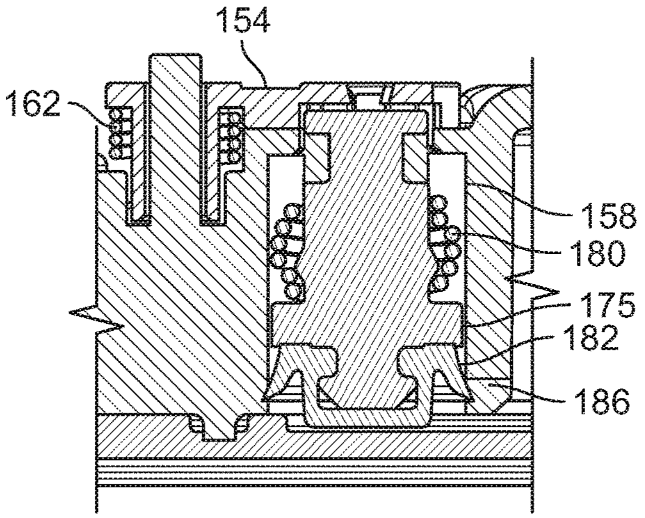
FIG. 22C is a cross-sectional view of the vent valve assembly and vent port of FIG. 22B in a de-pressurized configuration after the injection device button has been pushed.

After the final venting stage, the pressure within the expansion chamber 12 is at atmospheric so that there is no longer pressure pushing up on the bottom of the annular seal 182 of the pressure relief piston 175. As a result, the compression spring 180, as illustrated in FIG. 22C, is free to further expand and the piston head drops downwards with respect to the pivot plate 154. As this occurs, the stop 188 (FIG. 21) slides down and off of the pivot plate stop surface (168 of FIG. 21). With reference to FIGS. 21 and 22C, piston arms 176*a* and 176*b* then drop down through opposing slots 174*a* and 174*b* and clear of the pivot plate 154 as the compression spring further expands. With the piston arms 176*a* and 176*b* clear of the pivot plate 154, the pivot plate further turns in the direction of arrow 164 of FIG. 19 due to the urging of torsion spring 162 (FIGS. 19 and 22A-22C). As a result, the latching notch 184 (FIG. 21) of the pivot plate 154 pivots off of the locking tab 152 (FIG. 3) of the button 10 so that the button is released and rises upwards or extends back and the injection cannula 6 rises upward or retracts into the positions illustrated in FIG. 13A. The injection is then complete.

In summary, for the embodiment illustrated in FIGS. 13A-22C, use of the injection device would be as follows. The user removes the injection device from the package. The safety strip and adhesive liner are in place. The user removes the liner and attaches the device to their skin. The user removes the safety strip and pushes the injection device button. Pushing the button punctures the canister. The compressed gas in the canister fills the expansion chamber. With an expansion chamber of 0.75 to 1 cc of compressed gas at 150-200 psi, the gas expands into the expansion chamber that is approximately twice the volume of the vial. For example, theoretically and neglecting losses, a 1 cc canister at 150 psi fills a 10 cc expansion chamber to 15 psi. An expansion chamber of 10 cc at 15 psi fills a 10 mL vial with final pressure of approximately 7.5 psi. These expansion chambers sizes and pressures limit the pressure that the user is exposed in the event of balloon rupture.

Once the canister is punctured and gas fills the expansion chamber and the spring-loaded cannula holder is advanced at least partially through piston action from the compressed gas to a locked deployed position. Locking occurs from the vent valve assembly due to the pressure in expansion chamber. Once the cannula holder reaches the deployed position, this opens up the ability for the gas to pass to the spike holder. The spike holder is advanced with a piston interacting with the compressed gas until it reaches a deployed position within the vial through the stopper. At the deployed position, the gas pushes out the balloon into the vial and starts inflation. Fluid flows out of the vial due to the increasing size of the balloon. Dead space in the filter line and filter is exhausted through the hydrophobic filter. Fluid from the vial travels through the filter line through the hydrophobic/hydrophilic filter. Fluid passes through the hydrophilic into the cannula line and into the patient. Air flows through the hydrophobic into the environment. At the end of delivery the vent valve opens. This releases the air in the expansion chamber and releases the button to retract the injection cannula and the button is raised.

Figure 23:
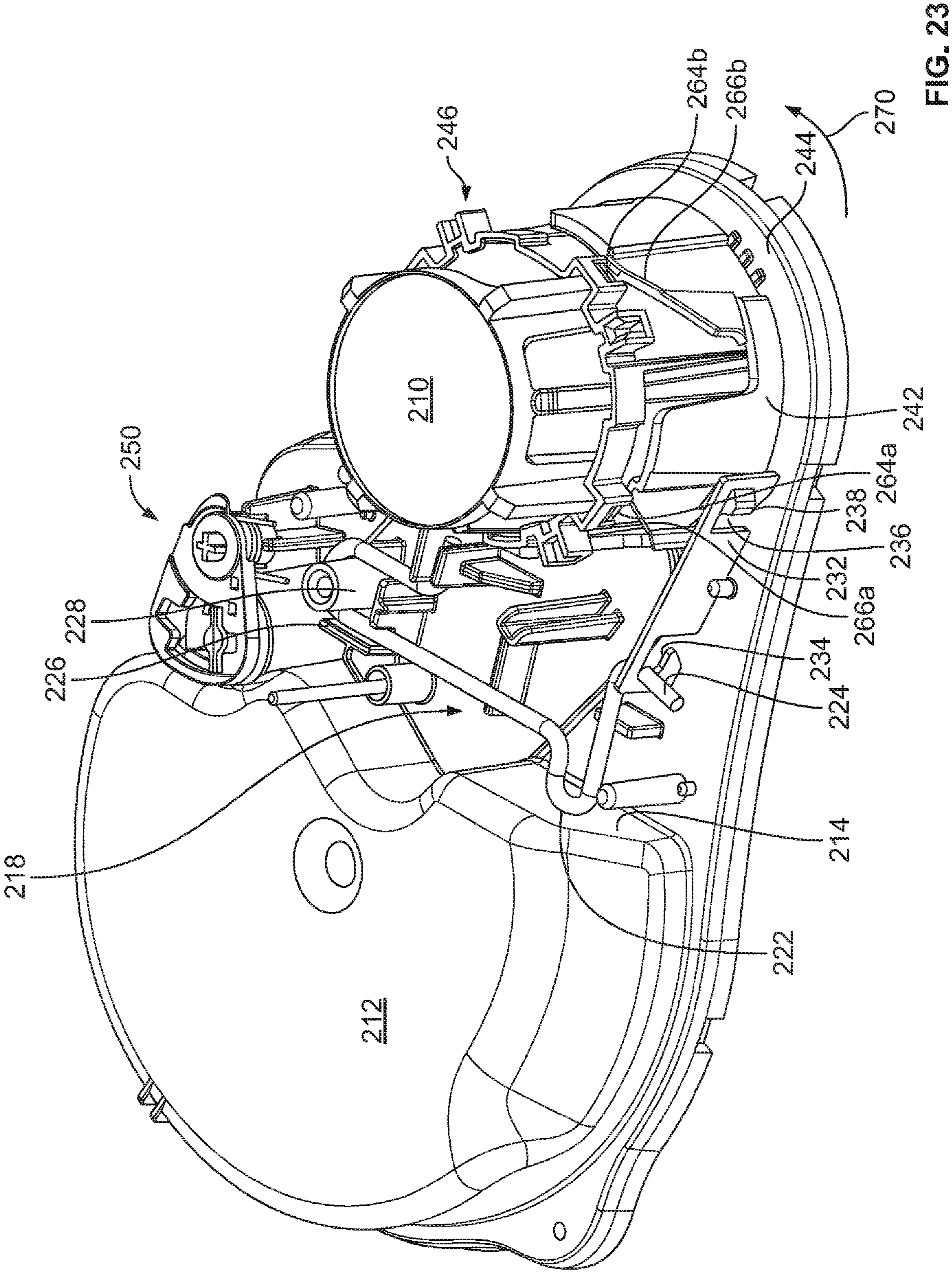
FIG. 23 is a perspective view of a mechanism to pierce the pressurized gas cartridge in an alternative embodiment of the disclosure.
Figure 24:
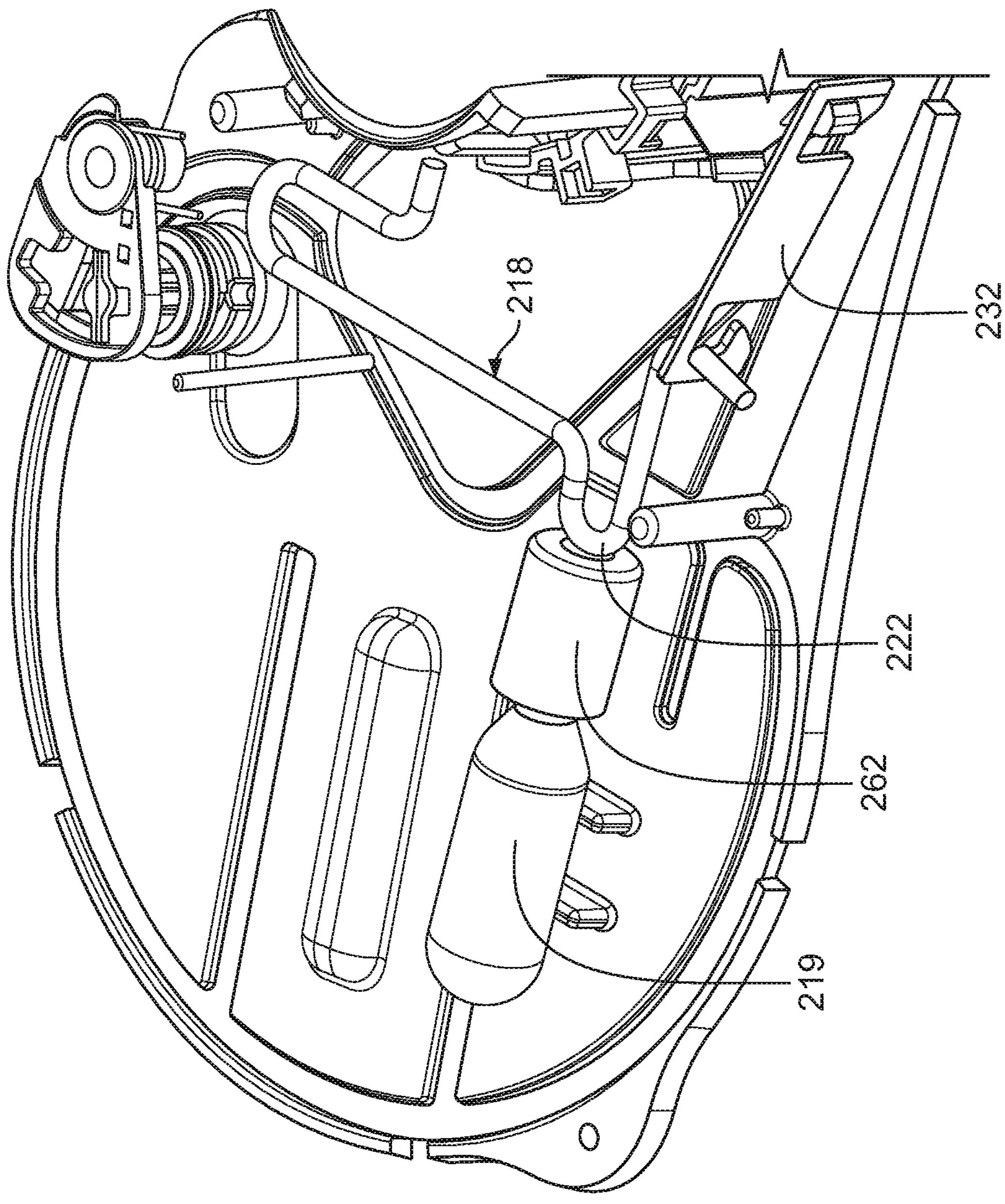
FIG. 24 is a partial view of the mechanism of FIG. 23 with the gas expansion chamber cover removed.

An alternative arrangement for puncturing the pressurized gas canister via actuation of the injection device push button is shown in FIGS. 23 and 24.

With reference to FIG. 23, a gas expansion chamber housing 212 includes a flexible wall portion 214. As an example only, the flexible wall portion 236 may be constructed of plastic with a thickness of approximately 0.030" for flexibility. Expansion chamber 212 is configured to supply pressurized gas to the cylinders 101 and/or 110 of FIGS. 13A and 13B, the balloon 5 (FIGS. 9-12) or 122 (FIGS. 18A-18C) and any other components of the injection device that receive pressurized gas as described above. The expansion chamber is provided with a vent valve assembly 250 that operates in the same manner as explained above for vent valve assembly 150 of FIGS. 19-22C.

A trigger spring, indicated in general at 218, includes a hammer portion 222 and a latch portion 224. A bracket 226 and a retainer post 228 cooperate to secure the retainer portion of the proximal end of the trigger spring in place in a fixed manner. The hammer portion 222 is urged into engagement with the flexible wall portion 216 of the gas expansion chamber 212 by the resilient forces of the trigger spring, as illustrated in FIG. 23. As examples only, the trigger spring 218 may be made of metal or steel.

With continued reference to FIG. 23, a link 232 includes a first notch 234 and a second notch 236. The first notch 234 is engaged by the latch portion 224 on the distal end of the trigger spring 218. The second notch 236 is engaged by a link hook 238 formed on or secured to a cam ring 242, with is rotatably positioned around a button shaft or socket, indicated in general at 246, that is fixed to base 244. As an example only, the link may be made of steel, metal or plastic.

As illustrated in FIG. 24, a gas cartridge cap 262 features an inner surface that holds a puncture tip having a sharp point. The cap 262 holds the puncture tip in a position where the puncture tip opposes a seal of the pressurized gas cartridge 219, which is positioned within the gas expansion chamber 212.

As revealed by a comparison of FIGS. 23 and 24, the cap 262 is positioned adjacent to, and in engagement with, an inner surface of the flexible wall portion 214 at a location that corresponds to the location where the hammer portion 222 of the trigger spring engages the flexible wall portion. As a result, the flexible wall portion 214 is sandwiched between the pressurized gas canister cap 262 and the hammer portion 222 of the trigger spring 218.

With reference to FIG. 23, camming hooks 264*a* and 264*b* are formed on the side of button 210. Camming ramps 266*a* and 266*b* are formed on rotating cam ring 242. When the button 210 is in the raised or extended position illustrated, the camming hooks 264*a* and 264*b* are positioned at the top of the camming ramps 266*a* and 266*b*.

As button 210 is pushed down, so that the button lowers and retracts into the socket 246, the camming hooks 264*a* and 264*b* travel down the corresponding camming ramps

266*a* and 266*b* of the cam ring so that the cam ring rotates in the direction of arrow 270 of FIG. 23 (i.e. counterclockwise).

As the cam ring 242 rotates in the direction of arrow 270 (FIG. 23), the link 232 is pulled by the hook 238. As a result, the hammer portion 222 of the trigger spring is pulled away from the flexible wall portion 214 of the gas expansion chamber against the urging of the trigger spring. This occurs until the latch portion 224 of the trigger spring slides out of the first notch 234 of the link 232 so that the deflected hammer portion 222, which is now spaced from the flexible wall portion 214, is released.

The released hammer portion 222, due to the resilient forces acting on the deflected trigger spring, impacts the flexible wall portion as the hammer portion springs back to its original position. This forces the central area of the flexible wall portion 214, and thus the puncture tip of cap 262 (FIG. 24) to move inwards and puncture the seal of the pressurized gas cartridge 219. In doing so, the flexible wall portion elastically deforms in a concave fashion into the gas expansion chamber 212. As a result, pressurized gas from the gas cartridge fills the gas expansion chamber 212 and flows to the components noted above.

It should be noted that in alternative embodiments, the flexible wall may be used to propel the gas cartridge towards a stationary puncture tip to puncture the seal of the pressurized gas cartridge.

While the preferred embodiments of the disclosure have been shown and described, it will be apparent to those skilled in the art that changes and modifications may be made therein without departing from the spirit of the disclosure, the scope of which is defined by the following claims.

What is claimed is:

1. An injection device comprising:

a. a vial holder configured to hold a vial containing a medical fluid;

b. a canister holder configured to hold a compressed gas canister;

c. a balloon;

d. a balloon spike in fluid communication with the balloon and configured to be inserted into a vial positioned in the vial holder and to selectively communicate with the compressed gas canister positioned within the canister holder so that the balloon is inflated within the vial to pressurize medical fluid within the vial;

e. an injection spike configured to be inserted into a vial positioned in the vial holder;

f. an injection cannula in fluid communication with the injection spike so that medical fluid pressurized in the vial by inflation of the balloon flows through the injection cannula;

g. a vial spike holder, where the balloon spike and the injection spike are secured to the vial spike holder and the vile spike holder is configured to move from a first position where the balloon and injection spikes are spaced from the vial and a second position where the balloon and injection spikes are inserted into the vial; and h. a holder driver including a gear rack connected to the actuation button, a gear rotatably mounted within the housing and a cam secured to the gear, where the gear rack engages and turns the gear as the actuation button moves from the first position to the second position so that the vial spike holder is moved from the first position to the second position by the cam.

2. The injection device of claim 1 wherein the balloon is configured to be positioned within a lumen of the balloon spike during insertion into the vial.

3. The injection device of claim 1 further comprising the vial containing the medical fluid positioned within the vial holder.

4. The injection device of claim 1 further comprising the compressed gas canister positioned within the canister holder.

5. The injection device of claim 1 further comprising the vial containing the medical fluid positioned within the vial holder and the compressed gas canister positioned within the canister holder.

6. The injection device of claim 5 wherein the vial includes a vial stopper which is pierced by the balloon spike and the injection spike as the balloon spike and the injection spike are inserted into the vial.

7. The injection device of claim 5 wherein the balloon is positioned within a lumen of the balloon spike during insertion into the vial.

8. The injection device of claim 1 wherein the balloon spike and the injection spike comprises a single dual lumen vial spike.

9. The injection device of claim 1 wherein the vial includes a distal wall or bottom and a stopper that is pierced by the injection spike when the injection spike is inserted into the vial and the balloon is configured to initially expand against the distal wall or bottom and then expand in a direction towards the stopper during inflation.

10. The injection device of claim 1 wherein the balloon includes axial grooves when inflated.

11. The injection device of claim 1 further comprising a hydrophilic and hydrophobic filter configured to receive fluid from the injection spike and deliver filtered fluid to the injection cannula.

12. A transfer device for transferring medical fluid from a vial comprising:

a. a vial holder configured to hold a vial containing a medical fluid;

b. a canister holder configured to hold a compressed gas canister;

c. a balloon;

d. a balloon spike in fluid communication with the balloon and configured to be inserted into a vial positioned in the vial holder and to selectively communicate with the compressed gas canister positioned within the canister holder so that the balloon is inflated within the vial to pressurize medical fluid within the vial;

e. an injection spike configured to be inserted into a vial positioned in the vial holder;

f. a transfer conduit in fluid communication with the injection spike so that medical fluid pressurized in the vial by inflation of the balloon flows through the transfer conduit;

g. a vial spike holder, where the balloon spike and the injection spike are secured to the vial spike holder and the vile spike holder is configured to move from a first position where the balloon and injection spikes are spaced from the vial and a second position where the balloon and injection spikes are inserted into the vial; and h. a holder driver including a gear rack connected to the actuation button, a gear rotatably mounted within the housing and a cam secured to the gear, where the gear rack engages and turns the gear as the actuation button moves from the first position to the second position so that the vial spike holder is moved from the first position to the second position by the cam.

13. The transfer device of claim 12 wherein the balloon is configured to be positioned within a lumen of the balloon spike during insertion into the vial.

* * * * *